United States Patent [19]
Wada et al.

[11] Patent Number: 4,720,576
[45] Date of Patent: Jan. 19, 1988

[54] PROCESS FOR DIMERIZATION OF AROMATIC HALIDE COMPOUNDS

[75] Inventors: Keisuke Wada, Yokohama; Keiichi Sato, Tokyo, both of Japan

[73] Assignee: Mitsubishi Chemical Industries Limited, Tokyo, Japan

[21] Appl. No.: 908,998

[22] Filed: Sep. 18, 1986

[30] Foreign Application Priority Data

Sep. 25, 1985 [JP] Japan ................................ 60-211296

[51] Int. Cl.$^4$ .................. C07C 51/353; C07C 143/24; C07C 102/00; C07C 41/30; C07C 37/11; C07C 1/26; C07C 120/00
[52] U.S. Cl. ................................ 562/481; 260/505 R; 260/505 C; 558/360; 558/411; 562/488; 564/155; 568/643; 568/730; 568/739; 585/427
[58] Field of Search ................ 562/481, 488; 585/427; 558/360, 411; 564/155; 568/643, 730, 739; 260/505 R, 505 C

[56] References Cited

U.S. PATENT DOCUMENTS 2,809,210 10/1957 Short et al. .......................... 562/488
4,105,705 8/1978 Larock ................................ 562/488

OTHER PUBLICATIONS

Busch et al., *Berichte* 62, 2612–2620, (1929).
Mayo et al, *J. Am. Chem. Soc.*, 71, 776–779, (1949).
Julia et al, *Bull. Soc. Chim. Fr*, 2791–2794, (1973).
Clark et al, *J.C.S. Perkin I*, 121–125, (1975).
BAJ Accession No. 22566C/13, 2-14-1980.

*Primary Examiner*—Werren B. Lone
*Assistant Examiner*—Vera C. Clarke
*Attorney, Agent, or Firm*—Jordan B. Bierman

[57] ABSTRACT

A process for dehalogeno-dimerization reaction of an aromatic halide compound which comprises dimerizing aromatic halide compound having at least one halogen atom attached to a carbon atom in the aromatic nucleus, and optionally having a substituent other than the halogen atom, in the presence of a platinum group metal catalyst, carbon monoxide, and an alkali metal compound and/or an alkaline earth metal compound.

23 Claims, No Drawings

PROCESS FOR DIMERIZATION OF AROMATIC HALIDE COMPOUNDS

BACKGROUND OF THE INVENTION

The present invention relates to a process for preparing an aromatic dimeric compound by dehalogeno-dimerizing aromatic halide compound.

FIELD OF THE INVENTION

Aromatic dimeric compounds are useful as industrial starting materials. Among biphenyl compounds, for example, alkali metal salts of 3,4,3',4'-biphenyltetracarboxylic acid are useful as starting materials for production of heat resistant polyimide resins. For preparation of aromatic dimeric compound by dehalogenodimerizing aromatic halide compound, for example, a method of dehalogeno-dimerizing the aromatic halide compound in an alkali hydroxide solution in the presence of a catalyst comprising metallic palladium supported on a carrier and methanol is known as described in J. Am. Chem. Soc., 71, 776 (1949), Japanese Patent Examined Publication No. 14015/84 and so forth. These known methods, however, have a disadvantage in that the yield of the desired aromatic dimeric compound is low because a large amount of aromatic compounds resulting from dehalogenation of aromatic halide compounds are by-produced. Thus, in order to obtain the desired dimer in high yield, it is necessary to inhibit the formation of dehalogenation by-products.

The present invention is intended to provide a process whereby aromatic dimeric compound can be prepared in high yield by dehalogeno-dimerizing aromatic halide compound.

SUMMARY OF THE INVENTION

The gist of the present invention resides in a process for dehalogeno-dimerization of an aromatic halide compound which comprises dehalogeno-dimerizing aromatic halide compound containing at least one halogen atom attached to a carbon atom in the aromatic nucleus, and optionally having a substituent other than the halogen atom, in the presence of a platinum group metal catalyst, carbon monoxide, and an alkali metal compound and/or an alkaline earth metal compound.

DETAILED DESCRIPTION OF THE INVENTION

The starting material to be used in the process of the present invention is an aromatic halide compound containing at least one halogen atom attached to a carbon atom of the aromatic nucleus.

The aromatic ring of the aromatic halide compound according to the present invention is not critical, usually a benzene ring or a naphthalene ring is included. Examples of the halogen atom are chlorine, bromine and iodine. Of these elements, bromine and chloride are preferred. The number of halogen atoms which can be linked to the carbon atoms in aromatic nucleus is 1 to 6, preferably 1 to 3. When the number of halogen atoms is 2 or more, these halogen atoms may be the same or different. The aromatic halide compound may be substituted in the aromatic nucleus by a substituent other than the halogen atom, without exerting adverse influences on the dehalogeno-dimerization reaction. When, however, the aromatic halide compound has a substituent other than the halogen atom at a carbon atom adjacent to that in which the halogen atom is positioned, the yield of the desired dimer tends to drop.

Examples of the substituent other than the halogen atom are a phenyl group, a hydroxyl group, an alkoxy group, a carbamoyl group, an amino group, a benzoyl group, an alkylcarbonyl group, a cyano group, an alkyl group, a $-SO_3H$ group, a $-SO_3Na$ group, a carboxyl group and a $-COONa$ group and so on. Preferably, the substituent are a phenyl group, a hydroxyl group, a $C_1-C_4$ lower alkoxyl group, a carbamoyl group, an amino group, a benzoyl group, a $C_1-C_4$ lower alkylcarbonyl group, a cyano group, a $C_1-C_4$ lower alkyl group, a $-SO_3H$ group, a $-SO_3Na$ group, a carboxyl group and a $-COONa$ group. The number of substituents varies within the range of 1 to 5 depending on the number of halogen atoms. When the aromatic halide compound has a substituent other than the halogen atom, the number of substituents is preferably 1 or 2. When the number of substituents is 2 or more, the substituents may be the same or different.

Particularly preferred examples of the aromatic halide compound are aromatic monohalide compound which may have a substituent other than the halogen atom in the meta-position and/or the para-position with respect to the halogen atom.

Representative examples of the aromatic halide compounds that are used in the present invention are chlorobenzene, bromobenzene, p-chlorobromobenzene, p-chlorodiphenyl, p-chlorophenol, p-chloroanisole, p-chlorophenetole, p-chlorobenzamide, p-chloroaniline, p-chlorobenzophenone, p-chloroacetophenone, p-chlorobenzonitrile, p-chlorobenzenesulfonic acid sodium salt, α-chloronaphthalene, 4-chloro-o-xylene, p-chlorobenzoic acid, 4-chlorophthalic acid, the alkali metal salts of 4-chlorophthalic acid, 4-chlorophthalic anhydride, and 4,5-dichlorophthalic acid. It is to be noted that the present invention is not limited to the above aromatic halide compounds.

In the process of the present invention, an aromatic halide compound is usually used alone. If necessary, however, a mixture of different aromatic halide compounds may be used.

Metals constituting the platinum group metal catalyst which is used in the present invention include palladium, rhodium, ruthenium, platinum and iridium. Of these elements, palladium and rhodium are suitable.

The platinum group metal catalyst is used in the form of an inorganic acid salt, such as a halide, a nitrate, a sulfate and the like; a salt of organic acid, such as an acetate, a benzoate, a phthalate and the like, a chelate salt containing β-diketones such as acetylacetone, etc. and a metal. Of these compounds, metal supported on a carrier, such as activated carbon, silica, alumina, silica-alumina, zeolite, titanium oxide, magnesia, diatomaceous earth, graphite, asbestos, an ion exchange resin, barium carbonate, calcium carbonate and the like are preferred. Particularly preferred is a catalyst comprising a metal supported on activated carbon. In these metal catalysts supported on a carrier, the amount of the metal supported on the carrier is usually 0.1 to 20 wt%, preferably 0.5 to 10 wt% based on the weight of the carrier. The amount of the platinum group metal catalyst used is usually 100 to 0.001 mmol, preferably 30 to 0.01 mmol (calculated as a metal atom) per mol of the aromatic halide compound regardless of the form of the catalyst.

In the dehalogeno-dimerization of the present invention, it is essential that carbon monoxide is present in the reaction system. Although the carbon monoxide pressure is not critical, partial pressure of the carbon monoxide is usually 0.001 to 150 kg/cm$^2$, preferably 0.1 to 60 kg/cm$^2$ and more preferably 1 to 10 kg/cm$^2$.

In order to maintain carbon monoxide in the dehalogeno-dimerization zone under the above-specified partial pressure, it is preferred to supply carbon monoxide in a gas form. It is also possible that carbon monoxide is supplied in such a manner that carbon monoxide is formed in situ in the reaction zone. For example, carbon monoxide can be supplied in the form of a carbonyl complex of Group VIII metal. The carbon monoxide gas is not always required to be pure and may contain nitrogen, hydrogen and so forth.

Although the action of carbon monoxide in the dehalogeno-dimerization reaction of the present invention is not clear, it is considered that the carbon monoxide has a certain action on the catalytic activity.

In the process of the present invention, an alkali metal compound and/or an alkaline earth metal compound is used as a halogen receptor. This halogen receptor is needed to form the desired aromatic dimeric compound in high yield. Representative examples of the alkali metal and alkaline earth metal compounds are salts of inorganic acid (e.g., carbonate, nitrate, phosphate, borate, etc.), hydroxides, salts of organic acid (e.g., acetate and phthalate, etc.), and alkoxides of alkali and alkaline earth metals.

Particularly preferred examples are hydroxides such as lithium hydroxide, sodium hydroxide, potassium hydroxide, magnesium hydroxide, calcium hydroxide, and barium hydroxide; carbonates such as sodium carbonate, potassium carbonate and sodium hydrogencarbonate; and alkoxides such as sodium methoxide, sodium ethoxide, and potassium tert-butylate. Hydroxides are particularly preferred from a viewpoint of a yield of the dehalogeno-dimerizaion reaction.

The amount of the halogen receptor used is not critical; it varies with the number of halogen atoms contained in the aromatic halide compound as the starting material and the presence of an acidic substituent such as a carboxyl group. The amount of the halogen receptor used is usually 0.01 to 100 mol, preferably 0.1 to 20 mol based on a mol of the aromatic halide compound.

The process of the present invention may be carried out in the presence or absence of a solvent depending on the type of the aromatic halide compound as the starting material. In a case where a solvent is used, solvents not exerting adverse influences on the reaction may be acceptable. Solvents which can be used include ether compounds such as tetrahydrofuran, and dioxane, ketone compounds such as acetone, diethyl ketone, methyl ethyl ketone, and cyclohexanone; ester compounds such as ethylene glycol diacetate; and water and so on.

In a case where a solvent is used, the amount of the solvent used is not critical; it is usually 0.01 to 100 parts by volume based on a part by volume of the aromatic halide compound.

In the process of the present invention, it is preferred to use water in combination in order to prepare the aromatic dimeric compounds in high yield. The amount of water used is at least 0.01 mol, preferably at least 0.1 mol per mol of the aromatic halide compound as the starting material. There is no upper limit of water to be used because water may also be used as a solvent for the dehalogeno-dimerization reaction. Usually about 300 mol per mol of the aromatic halide compound may be used. Water can be added separately or as an aqueous solution in which the alkali metal compound, for example, is dissolved.

Although the exact reason why the yield is increased when water is used in combination is not clear, it is considered that water exerts a certain action on the catalytic activity together with carbon monoxide.

In the process of the present invention, a mixture of the above aromatic halide compound, platinum group metal catalyst, carbon monoxide, and alkali metal compound and/or alkaline earth metal compound is heated in the presence or absence of a solvent at a temperature of 20° to 300° C., preferably 50° to 200° C.

The reaction pressure is in a range of atmospheric pressure to 200 kg/cm$^2$, preferably atmospheric pressure to 100 kg/cm$^2$.

The process of the present invention may be carried out by any of the batchwise system, the semibatchwise system and the continuous system.

The platinum group metal catalyst used in the reaction is separated and recovered from the reaction mixture after the reaction by conventional techniques such as extraction, crystallization and reduction. When a metal catalyst supported on a carrier is used, the catalyst can be easily separated and recovered by filtration, and used again as a catalyst for the dehalogeno-dimerization reaction.

Aromatic dimeric compounds prepared by the process of the present invention are isolated from the reaction mixture by techniques such as vaporization, distillation, crystallization and acid precipitation, according to their physical properties.

In accordance with the process of the present invention, aromatic dimeric compounds can be prepared in high yield and with high selectivity by carrying out the dehalogeno-dimerization reaction in the presence of carbon monoxide, and thus the present invention is industrially very advantageous.

The present invention is described in greater detail with reference to the following examples, although it is not intended to be limited thereto.

EXAMPLE 1

15 ml of an aqueous solution of 0.2 g of 2 wt% palladium carbon, a mixture of 1.6 g of 4-chlorophthalic anhydride (hereinafter abbreviated to "4-CPA"), 0.3 g of phthalic anhydride and 0.05 g of dichlorophthalic anhydride, and 2 g of sodium hydroxide was placed in a 70-milliliter volume spinner stirring-type autoclave made of Hastelloy. After the atmosphere in the autoclave was replaced with carbon monoxide gas, carbon monoxide gas was introduced into the autoclave under pressure to 5 kg/cm$^2$ (gauge pressure), and the reaction was conducted at 150° C. for 3 hours. A high speed liquid chromatographic analysis showed that a sodium salt of dehalogenated orthophthalic acid (hereinafter abbreviated to a "PA salt") and the desired sodium salt of 3,4,3',4'-biphenyltetracarboxylic acid (hereinafter abbreviated to "S-BTC salt") were formed in the reaction mixture. The results are shown in Table 1.

COMPARATIVE EXAMPLE 1

The procedure of Example 1 was repeated except that nitrogen gas was used in place of carbon monoxide gas. The results are shown in Table 1.

COMPARATIVE EXAMPLE 2

The procedure of Example 1 was repeated except that nitrogen gas was used in place of carbon monoxide gas, and 1.28 g of methanol was added to the reaction system. The results are shown in Table 1.

TABLE 1

|  | 4-CPA Conversion (mol %) | S-BTC Salt Yield *1 (mol %) | PA Salt Yield *2 (mol %) |
| --- | --- | --- | --- |
| Example 1 | 100 | 67 | 21 |
| Comparative Example 1 | 2.3 | 0.5 | 1.8 |
| Comparative Example 2 | 100 | 46 | 53 |

*1 S-BTC salt yield (%) =
$\frac{\text{Formed S-BTC salt (mmol)} \times 2}{\text{Charged 4-CPA salt (mmol)}} \times 100$

*2 PA salt yield (%) =
$\frac{\text{By-produced PA salt (mmol)}}{\text{Charged 4-CPA salt (mmol)}} \times 100$

EXAMPLE 2

A mixture of 0.6 g of 2 wt% palladium carbon, 4.8 g of 4-CPA, 0.98 g of phthalic anhydride and 0.15 g of dichlorophthalic anhydride, 9 g of sodium hydroxide and 50 ml of water were placed in a 200-milliliter electromagnetic induction type rotary autoclave made of stainless steel, and the atmosphere in the autoclave was replaced with nitrogen gas and the temperature was raised to 100° C. At 100° C., carbon monoxide gas was introduced to reach 2 kg/cm² of gauge pressure through a pressure controller from a tank, and the reaction was carried out for 10 hours at a constant pressure. The reaction mixture was analyzed in the same manner as in Example 1. The results are as follows.

| 4-CPA Conversion | 100% |
| --- | --- |
| S-BTC salt yield | 80.5% |
| PA salt yield | 15.2% |

EXAMPLES 3 TO 5

The procedure of Example 1 was repeated except that a predetermined amount of each basic compound shown in Table 2 was used in place of sodium hydroxide as the halogen receptor. The results are shown in Table 2.

TABLE 2

|  | Basic Compound | | 4-CPA Conversion (mol %) | S-BTC Salt Yield (per Charged 4-CPA) (mol %) |
| --- | --- | --- | --- | --- |
|  | Type | Amount (g) | | |
| Example 3 | Potassium hydroxide | 2.8 | 100 | 63.2 |
| Example 4 | Lithium hydroxide (monohydrate) | 2.1 | 88.3 | 56.6 |
| Example 5 | Sodium carbonate | 2.65 | 27.2 | 14.2 |

EXAMPLE 6

1.0 g of 2 wt% palladium carbon, 7.83 g of metha-chlorobenzoic acid (hereinafter abbreviated to "CBA"), 10 g of sodium hydroxide and 50 ml of water were placed in a 100-milliliter volume electromagnetic induction type rotary autoclave made of stainless steel, and the atmosphere in the autoclave was replaced with carbon monoxide and the temperature was raised to 100° C. At 100° C., carbon monoxide gas was supplied to reach 1 kg/cm² of gauge pressure through a pressure controller from a tank, and was reacted at a constant pressure for 6 hours. After the completion of reaction, the reaction mixture was analyzed in the same manner as in Example 1. The yield of the desired sodium salt of biphenyl-3,3'-dicarboxylic acid (hereinafter abbreviated to a "BDC salt") was 80%, and the yield of the sodium salt of dehalogenated benzoic acid (hereinafter abbreviated to a "BA salt") was 16%. The yields of the BDC salt and BA salt were calculated from the following equations.

$$BDC \text{ salt yield } (\%) = \frac{\text{Formed } BDC \text{ salt (mmol)} \times 2}{\text{Charged } CBA \text{ (mmol)}} \times 100$$

$$BA \text{ salt yield } (\%) = \frac{\text{Formed } BA \text{ salt (mmol)}}{\text{Charged } CBA \text{ (mmol)}} \times 100$$

COMPARATIVE EXAMPLE 3

The procedure of Example 6 was repeated except that nitrogen gas was used in place of carbon monoxide gas. It was observed that no BDC salt was formed.

EXAMPLE 7

The procedure of Example 1 was repeated except that a solution of 1.126 g of chlorobenzene and 1 g of sodium hydroxide in a mixture of 7.5 ml of water and 7.5 ml of dioxane were used in place of 15 ml of the aqueous solution of a mixture of 1.6 g of 4-CPA, 0.3 g of phthalic anhydride and 0.05 g of dichlorophthalic anhydride, and 2 g of sodium hydroxide. The results are shown in Table 3.

EXAMPLES 8 TO 11

The procedure of Example 1 was repeated except that a solution of a predetermined amount of each aromatic halide compound shown in Table 3 and 1 g of sodium hydroxide in 15 ml of water were used in place of 15 ml of the solution of a mixture of 1.6 g of 4-CPA, 0.3 g of phthalic anhydride and 0.05 g of dichlorophthalic anhydride, and 2 g of sodium hydroxide. The results are shown in Table 3.

TABLE 3

|  | Aromatic Halide Compound | | Yield of Aromatic Dimeric Compound (per charged palladium)* (mol %) |
| --- | --- | --- | --- |
|  | Type | Amount (g) | |
| Example 7 | Chlorobenzene | 1.126 | 5878 |
| Example 8 | Bromobenzene | 1.57 | 2979 |
| Example 9 | α-Chloronaphthalene | 1.626 | 239 |
| Example 10 | 4-Chloro-o-xylene | 1.405 | 904 |
| Example 11 | p-Chlorophenol | 1.285 | 3697 |

*Yield of aromatic dimeric compound (%) =
$\frac{\text{Aromatic dimeric compound (mmol)}}{\text{Charged palladium (mg atom)}} \times 100$

EXAMPLE 12

The procedure of Example 8 was repeated except that 1.126 g of chlorobenzene and 1.06 g of sodium carbonate were used in place of bromobenzene and sodium hydroxide, respectively. The results are shown in Table 4.

COMPARATIVE EXAMPLE 4

The procedure of Example 12 was repeated except that nitrogen gas was used in place of carbon monoxide gas. The results are shown in Table 4.

TABLE 4

| | Aromatic Halide Compound | | Yield of Aromatic Dimeric Compound (per charged palladium) (mol %) |
|---|---|---|---|
| | Type | Amount (g) | |
| Example 12 | Chlorobenzene | 1.126 | 957 |
| Comparative Example 4 | Chlorobenzene | 1.126 | 13 |

EXAMPLE 13

The procedure of Example 1 was repeated except that 1.126 g of chlorobenzene, 3.16 g of barium hydroxide 8 hydrate and 15 ml of water were used in place of 15 ml of the aqueous solution of a mixture of 1.6 g of 4-CPA, 0.3 g of phthalic anhydride and 0.05 g of dichlorophthalic anhydride, and 2 g of sodium hydroxide.

The yield of biphenyl (based on the charged palladium) was 4474 mol%.

EXAMPLE 14

The procedure of Example 1 was repeated wherein 5 wt% rhodium-carbon was used in place of the palladium carbon.

The yield of S-BTC salt was 110 mol% (based on the charged rhodium).

While the invention has been described in detail and with reference to specific embodiments thereof, it will be apparent to one skilled in the art that various changes and modifications can be made therein without departing from the spirit and scope thereof.

What is claimed is:

1. A process for dehalogeno-dimerization reaction of at least one aromatic halide compound selected from the group consisting of 4-chlorophthalic acid, alkali metal salts of 4-chlorophthalic acid and 4-chlorophthalic anhydride which comprises dehalogeno-dimerizing the aromatic halide compound in the presence of a platinum group metal catalyst, carbon monoxide and an alkali metal compound and/or an alkaline earth metal compound, with or without a solvent.

2. The process as in claim 1, wherein metal component of the platinum group metal catalyst is at least one selected from the group consisting of palladium, rhodium, ruthenium, platinum and iridium.

3. The process as in claim 1, wherein the metal component of the platinum group metal catalyst is palladium or rhodium.

4. The process as in claim 1, wherein the platinum group metal catalyst is selected from the group consisting of the salts of inorganic acid, salts of organic acid, and chelate salts of platinum group metals, and platinum group metals.

5. The process as in claim 1, wherein the platinum group metal catalyst is a platinum group metal supported on a carrier.

6. The process as in claim 1, wherein the amount of the platinum group metal catalyst used is 100 to 0.001 mol calculated as metal atom, based on a mol of the aromatic halide compound.

7. The process as in claim 1, wherein the amount of the platinum group metal catalyst used is 30 to 0.01 mmol based on a mol of the aromatic halide compound.

8. The process as in claim 1, wherein a partial pressure of the carbon monoxide is 0.001 to 150 kg/cm$^2$.

9. The process as in claim 1, wherein a partial pressure of the carbon monoxide is 0.1 to 60 kg/cm$^2$.

10. The process as in claim 1, wherein a partial pressure of the carbon monoxide is 1 to 10 kg/cm$^2$.

11. The process as in claim 1, wherein the alkali metal compound and/or the alkaline earth metal compound is the hydroxide, salt of inorganic acid, salt of organic acid or alkoxide of the alkali metal or alkaline earth metal.

12. The process as in claim 1, wherein the alkali metal compound and/or the alkaline earth metal compound is the hydroxide or carbonate of the alkali metal or alkaline earth metal.

13. The process as in claim 1, wherein the alkali metal compound and/or the alkaline earth metal compound is selected from the group consisting of lithium, sodium, potassium and barium compounds.

14. The process as in claim 1, wherein the amount of the alkali metal compound and/or the alkaline earth metal compound is 0.01 to 100 mol based on a mol of the aromatic halide compound.

15. The process as in claim 1, wherein the amount of the alkali metal compound and/or the alkaline earth metal compound is 0.1 to 20 mol based on a mol of the aromatic halide compound.

16. The process as in claim 1, wherein the dehalogeno-dimerization reaction of the aromatic halide compound is carried out in the presence of water.

17. The process as in claim 16, wherein the amount of water is at least 0.01 mol based on a mol of the aromatic halide compound.

18. The process as in claim 16, wherein the amount of water is 0.1 to 300 mol based on a mol of the aromatic halide compound.

19. The process as in claim 1, wherein the dehalogeno-dimerization reaction is carried out with a solvent selected from the group consisting of ethers, ketones, esters, and water.

20. The process as in claim 1, wherein the dehalogeno-dimerization reaction is carried out at a temperature of 20° to 300° C.

21. The process as in claim 1, wherein the dehalogeno-dimerization reaction is carried out at a pressure of atmospheric pressure to 200 kg/cm$^2$.

22. A process for dehalogeno-dimerization reaction of an aromatic halide compound which comprises dehalogeno-dimerizing an aromatic halide compound having at least one halogen atom attached to a carbon atom in the aromatic nucleus, and optionally having a substituent other than the halogen atom selected from the group consisting of a phenyl group, a hydroxyl group, an alkoxy group, a carbamoyl group, an amino group, a benzoyl group, an alkylcarbonyl group, a cyano group, a sulfonic acid group, a —SO$_3$Na group, an alkyl group, a carboxyl group and a —COONa group, in the presence of a platinum group metal catalyst, carbon monoxide and an alkali metal compound and/or an alkaline earth metal compound, with or without a solvent.

23. A process for dehalogeno-dimerization reaction of at least one aromatic halide compound selected from the group consisting of chlorobenzene, bromobenzene, 4-chloro-o-xylene, p-chlorophenol, metachlorobenzoic acid, α-chloronaphthalene, alkali metal salts of 4-chlorophthalic acid, and 4-chlorophthalic anhydride which comprises dehalogeno-dimerizing the aromatic halide compound in the presence of a platinum group metal catalyst, carbon monoxide and an alkali metal compound and/or an alkaline earth metal compound, with or without a solvent.

* * * * *